United States Patent [19]

Ward

[11] 4,009,707
[45] Mar. 1, 1977

[54] AUTOMATIC ACOUSTIC IMPEDANCE METER

[75] Inventor: John W. Ward, Charlottesville, Va.

[73] Assignee: Teledyne Avionics, a division of Teledyne Industries Inc., Charlottesville, Va.

[22] Filed: July 29, 1975

[21] Appl. No.: 600,067

[52] U.S. Cl. ............................... 128/2 Z; 179/1 N
[51] Int. Cl.[2] ..................... A61B 5/12; A61B 10/00
[58] Field of Search ............ 128/2 Z, 2 R; 179/1 N

[56] References Cited

UNITED STATES PATENTS

| 3,295,513 | 1/1967 | Dippolito | 128/2 Z |
| 3,395,697 | 8/1968 | Mendelson | 128/2 Z |
| 3,757,769 | 9/1973 | Arguimbau et al. | 128/2 Z |
| 3,882,848 | 5/1975 | Klar | 128/2 Z |

OTHER PUBLICATIONS

McCandless, G. A. et al. *Trans. Amer. Acad. of Ophthalmology and Otolaryngology*, Mar.–Apr., 1974, vol. 78, pp. 97–102.

*Primary Examiner*—Kyle L. Howell

[57] ABSTRACT

In an acoustic impedance meter used for evaluating the performance of the middle ear and tympanic membrane system; a sound source is coupled to the ear canal by means of an ear probe and a sound sensor in conjunction with an inverse feedback system maintains a constant sound intensity in the ear canal regardless of ear canal compliance. An analog voltage, derived from the sound source excitation, is thereby representative of ear canal compliance. A pump is provided to moderately pressurize or evacuate the ear canal to determine the variation in compliance under various test pressures. An acoustic stimulus generator may be used to elicit an acoustic reflex response and a storage and comparison circuit derives an analog voltage representative of this acoustic reflex response.

5 Claims, 7 Drawing Figures

AUTOMATIC ACOUSTIC IMPEDANCE METER

SYSTEM BLOCK DIAGRAM

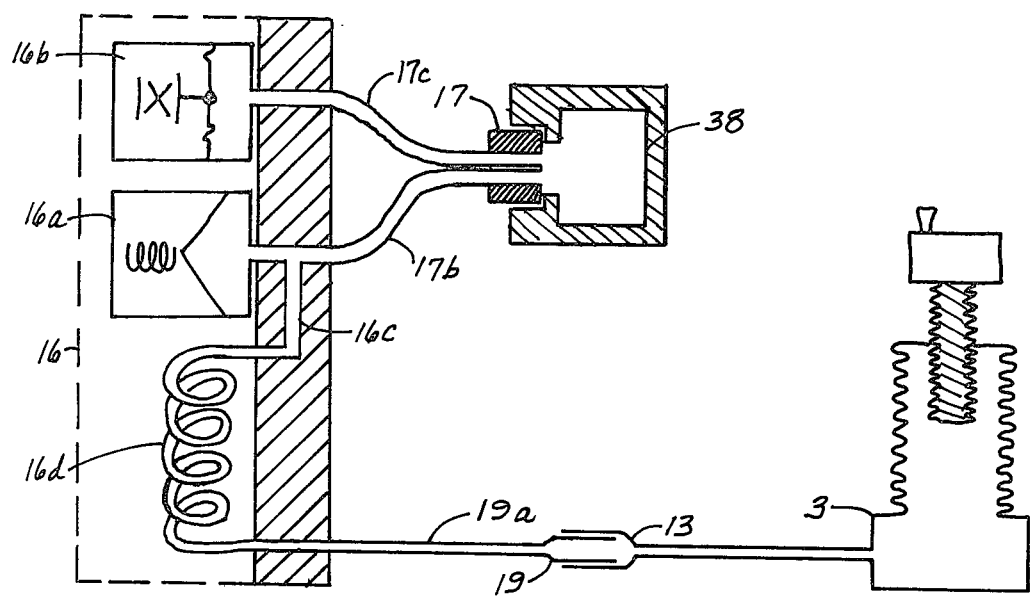
FIG 3 TRANSDUCER
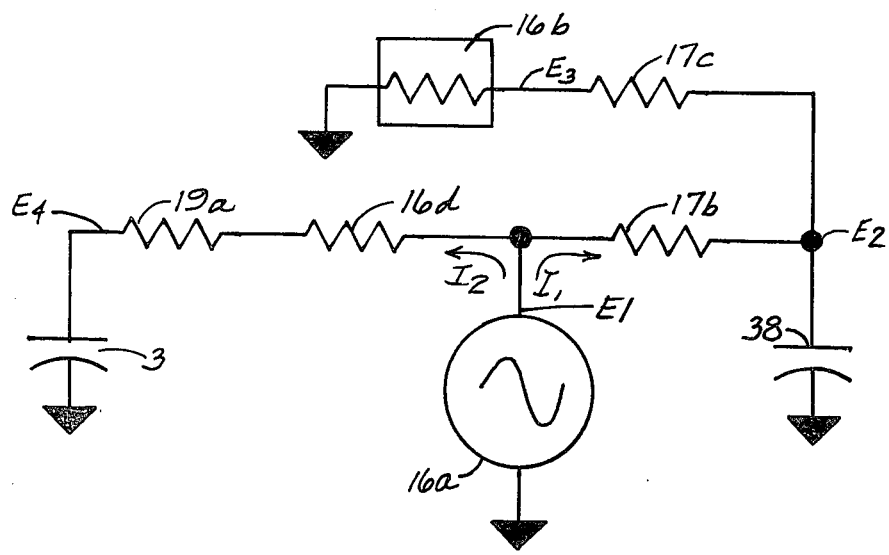
FIG 4 TRANSDUCER EQUIVALENT CIRCUIT

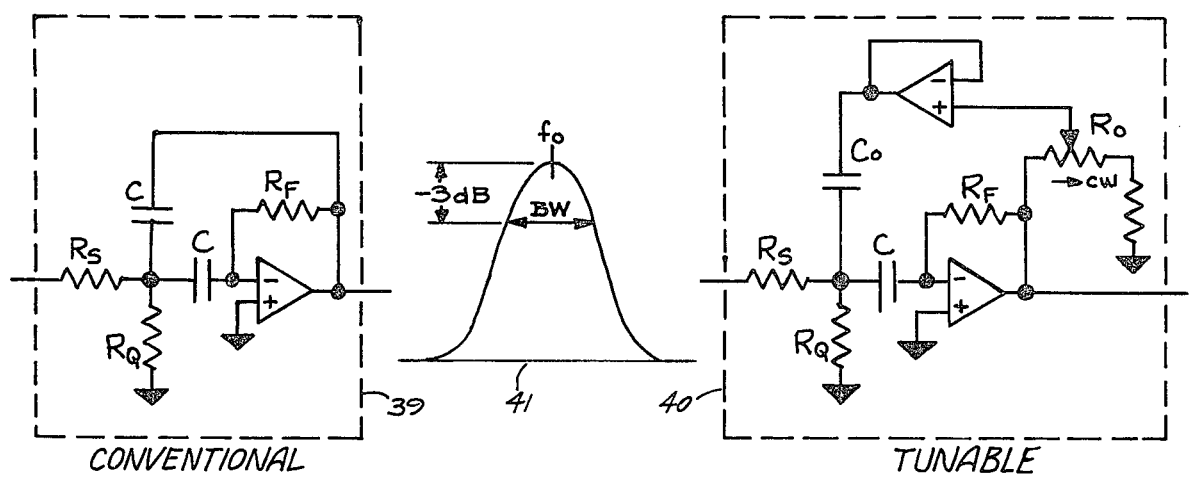
FIG 5 BAND PASS ACTIVE FILTER
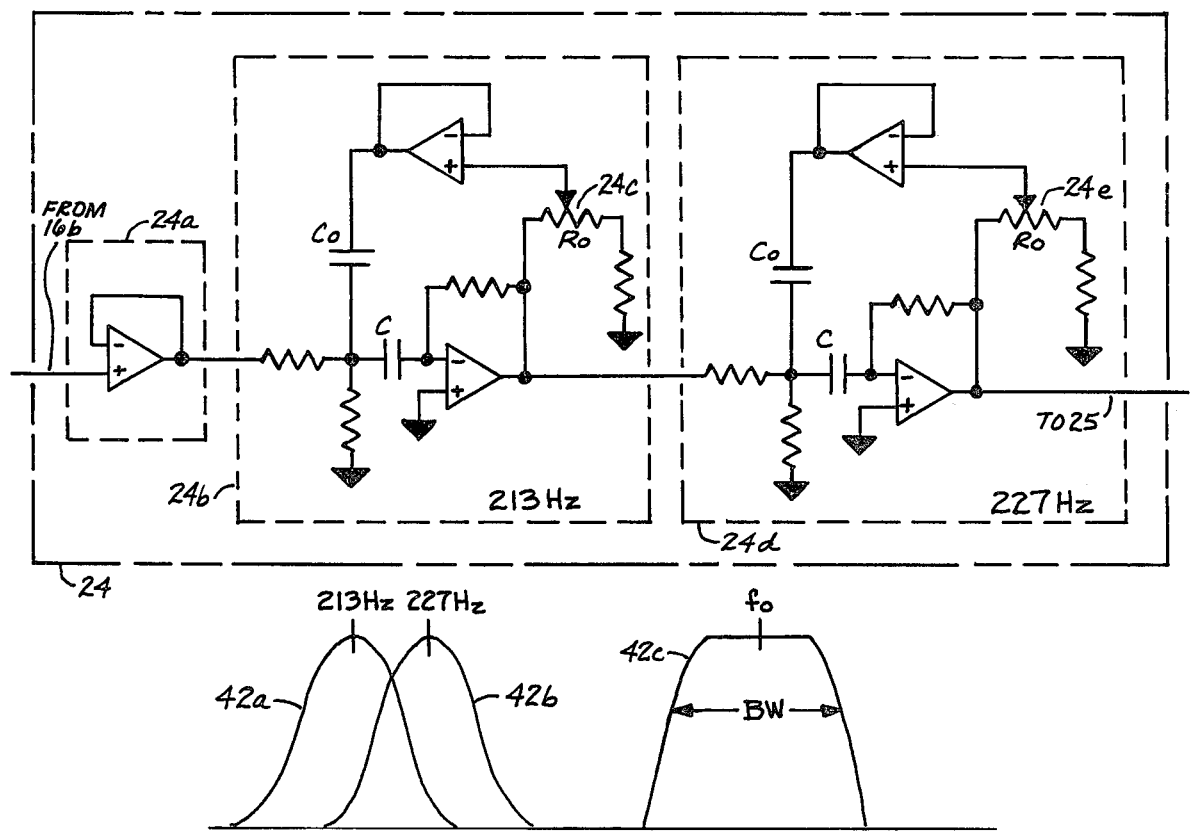
FIG 6 BAND PASS AMPLIFIER

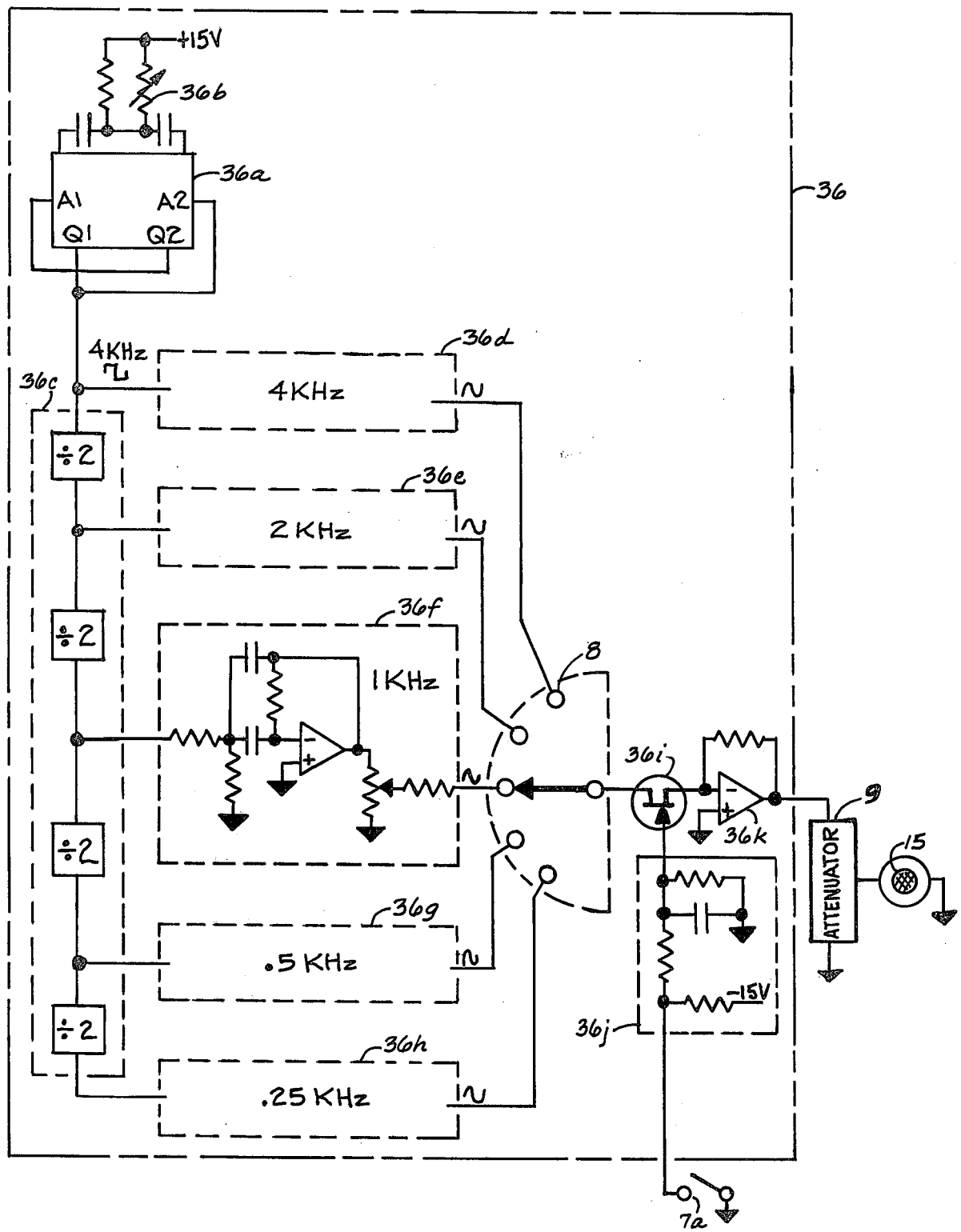
FIG 7 STIMULUS SYSTEM

AUTOMATIC ACOUSTIC IMPEDANCE METER

BACKGROUND OF THE INVENTION

An electro-acoustic impedance meter is an audiological instrument used to determine the performance of the middle ear system. The flexibility, or compliance, of the tympanic membrane and the mobility of the middle ear ossicular chain are measured as a combined system under various conditions or ear canal pressurization or evacuation and the compliance vs pressure data, thus obtained, may be plotted as the tympanogram for the tested ear. I subsequently refer to this combined complex compliance as ear canal compliance or simply compliance. The compliance measurement is based on the equivalent acoustical compliance of a hard-walled cavity and the usual unit of measurement is the equivalent volume expressed in cubic centimeters. Tympanometry is performed by inserting and sealing a pressure source, a sound source, and sound detector in the ear canal and evaluating the ear canal compliance as the ear canal pressure is adjusted. At a pressure of approximately +250mm $H_2O$, the tympanic membrane becomes essentially inelastic and the compliance measured at this pressure is termed the static, or base, compliance. As the ear canal pressure is decreased, a point of maximum, or peak, compliance occurs when the ear canal pressure is equivalent to the pressure existing in the subject's middle ear system. This pressure is termed the middle ear pressure. Further decrease in ear canal pressure again causes the tympanic membrane to become inelastic. The middle ear compliance is determined by subtracting the base compliance from the peak compliance. Middle ear compliance, middle ear pressure and the interrelationship between compliance and pressure are all of diagnostic significance.

If, at the point of peak compliance, the non-test, or contra-lateral ear is stimulated by a relatively loud sound, a contraction occurs in the muscles supporting the ossicular system, causing a partial stiffening of the tympanic membrane. This reaction is detected as a decrease in the measured compliance in the presence of the contra-lateral stimulus and is termed the acoustic reflex. The acoustic reflex is non-subjective and has diagnostic significance for both hearing and neurological problems.

My Automatic Electro-Acoustic Impedance Meter and other manually-operated electro-acoustic impedance meters seem to be misnamed, since both it and they operate by measuring the compliance, or equivalent volume, of the ear canal and tympanic membrane system. However, this terminology is in accordance with current American Speech and Hearing Association (ASHA) nomenclature and medical practice in the field, and stems from much earlier work done by purely acoustic methods.

Prior instruments in the impedance audiometry field are properly called impedance bridges, since they read the compliance magnitude by a complex manual bridge-balance technique, in which the balance control must be adjusted at each pressure setting and the compliance value read from a calibrated scale. These are cumbersome and slow to operate and due to the nature of the scales used, are difficult to read to a high precision. Prior instruments use a "3-tube" ear probe, employing individual flexible tubes for air pressure, sound source and sound detector, making the ear probe heavy and bulky. Prior instruments, employing the "3-tube" probe, exhibit significant acoustic coupling between the ear canal and the pressure pump system, thereby requiring electrical cancellation of a residual volume component in order to measure the relatively small, though significant, static compliance and middle ear compliance components. Prior instruments require manual balancing of the bridge system at the peak compliance point immediately before applying the contra-lateral stimulus in the measurement of the acoustic reflex. Prior instruments, due to the relatively broad frequency response to their sound detector amplifiers, respond to pulse beats, respiration, head movement and other unrelated influences.

It is therefore an object of my invention to provide an electro-acoustic impedance meter which is automatically maintained in balance by inverse feedback control.

It is another object of my invention to provide an electro-acoustic impedance meter which will display the results of its measurement in direct digital form, without reference to scales or the like.

It is another object of my invention to provide an electro-acoustic impedance meter employing capillary acoustic resistance means of isolation between the pressure system and the compliance measuring systems and thereby permitting the use of a lighter, smaller ear probe.

It is a further object of my invention to provide an electro-acoustic impedance meter which will display the presence of the acoustic reflex without prior balancing or other adjustment.

It is an additional object of my invention to provide an electro-acoustic impedance meter which includes narrow-band filter means to minimize the influences of head movement, pulse, breathing, etc. in the determination of compliance.

It is still another object of my invention to provide an electro-acoustic impedance meter which includes a wide range attenuator and tone source thereby permitting it to be used as a screening audiometer.

It is a general object of my invention to provide an electro-acoustic impedance meter which is simple and convenient to operate and is also reliable and rugged in construction to permit portable use.

IN THE DRAWINGS

FIG. 3 shows a detail of the mechanical design of the Transducer portion of my electro-acoustic impedance meter.

FIG. 4 shows an explanatory Transducer electrical Equivalent Circuit of the pneumatic system.

FIG. 5 is an electrical schematic of the Tunable Band-Pass Active Filter used in my electro-acoustic impedance meter and a Conventional Band-Pass Active Filter.

FIG. 6 is an electrical schematic of my 2-stage Band-Pass Amplifier.

FIG. 7 is an electrical schematic of the Stimulus System of my electro-acoustic impedance meter.

PREFERRED EMBODIMENT OF THE INVENTION

Figure 1:
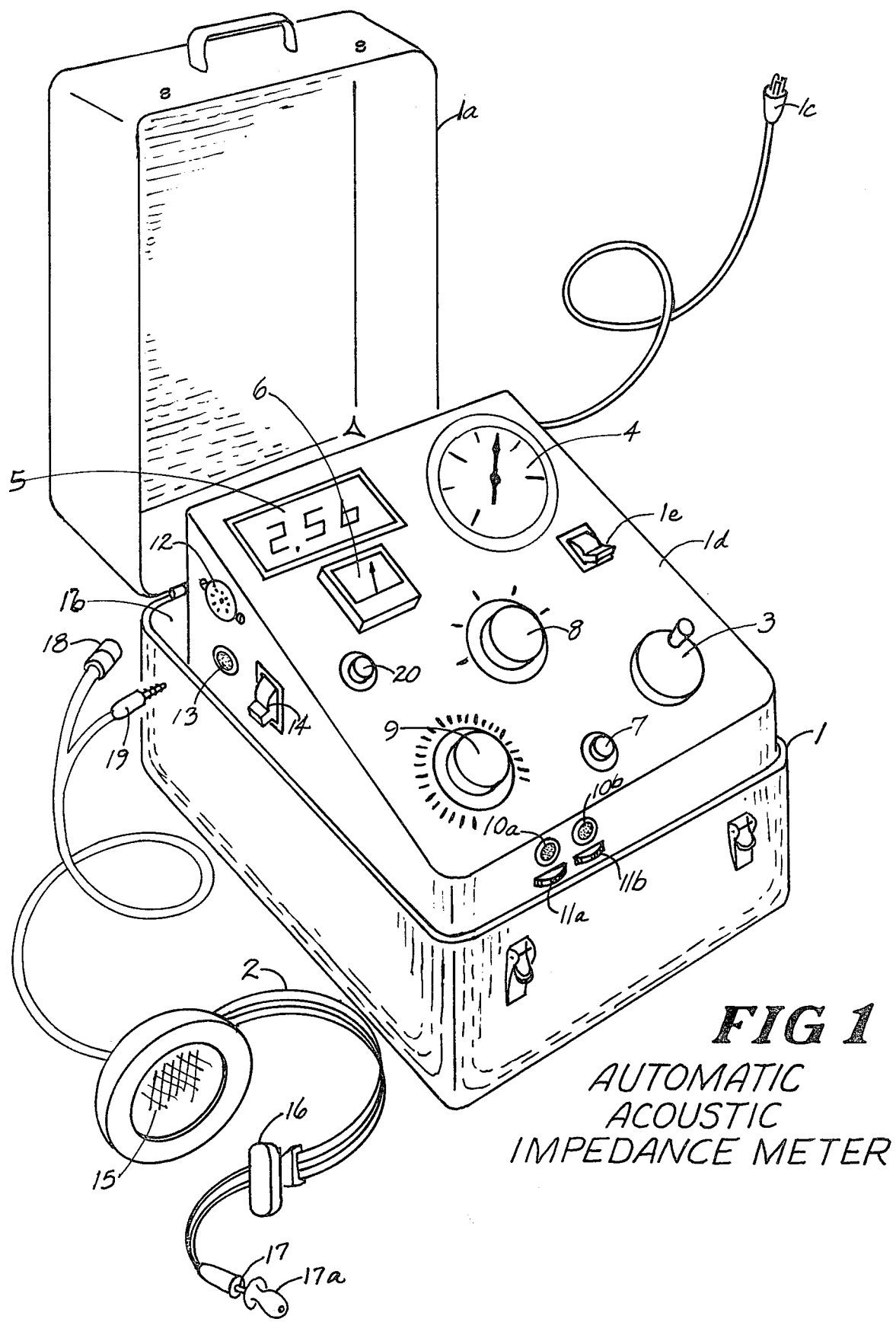
FIG. 1 is a perspective view of my Automatic Acoustic Impedance Meter with carrying case and associated headset, including electrical wiring and pressure tubing.

This invention had undergone several packaging modifications, with end result that the Automatic Acoustic Impedance Meter configuration shown in FIG. 1 is one preferred embodiment. In this Figure, the instrument assembly 1, has a hinged, removable cover 1a, and a compartment behind the instrument assembly 1b, which can be used for storage of the power cord 1c, the accessory headset 2, and the like. A pressure pump control 3, may be used to pressurize or evacuate the ear canal during test, and the resulting pressure is indicated on the gauge 4, reading both positive and negative pressures. The digital display 5, indicates the measured compliance value without further adjustments of any kind. The meter 6, indicates change in compliance when the stimulus control 7, is pressed. The stimulus frequency switch 8, and stimulus attenuator 9, may be set to control the stimulus conditions. Hard walled test cavities 10a, and 10b are used as compliance standards for self calibration. The calibration controls 11a and 11b permit adjustment of the instrument to read the exact volume of the test cavities in order to maintain overall instrument accuracy. The headset receptacle 12, provides for electrical connection of the headset to the instrument, while the pressure receptacle 13, allows connection of the headset pneumatic circuit. The probe tone switch 14, permits the ear probe tone to be suppressed when the instrument is used as a screening audiometer.

Returning to the headset 2, FIG. 1, the earphone 15, responds to the conditions of the stimulus controls 7, 8, and 9 to provide the contra-lateral stimulus required to evoke the acoustic reflex, or to apply the stimulus for use as a screening audiometer. The headset transducer assembly 16, is fitted with an ear probe 17, which in turn is fitted with a flexible probe tip 17a, which is inserted in the ear canal during test. The headset electrical plug 18, mates with the receptacle 12, and the headset pressure plug 19, mates with the receptacle 13, to connect the headset, both electrically and pneumatically, to the instrument. A power switch 1e, controls a power source. The pressure release 20, vents the pressure system to ambient air when manually actuated.

Figure 2:
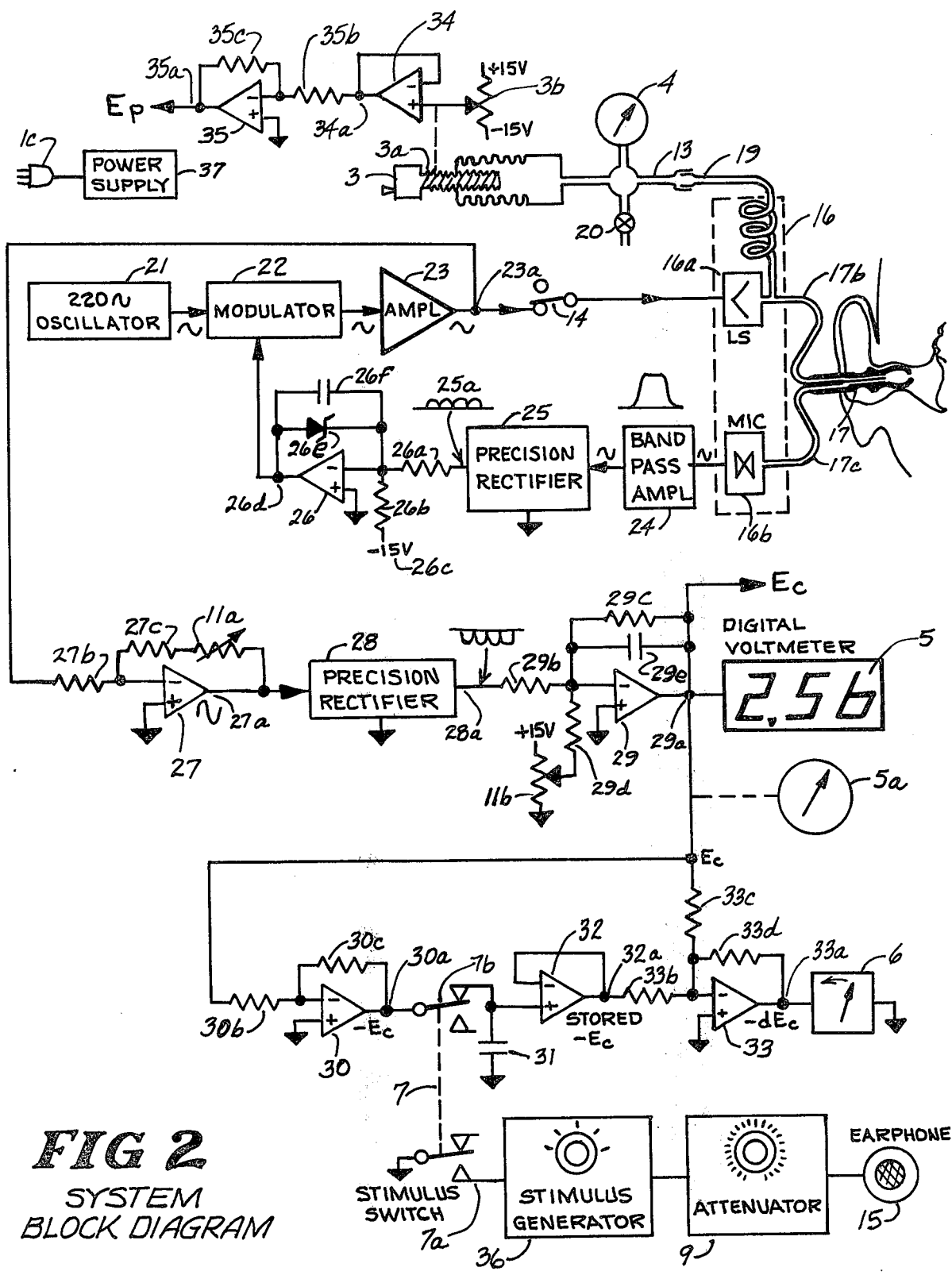
FIG. 2 is a System Block Diagram of my device.

The System Block Diagram, FIG. 2, is an overall functional diagram of my electro-acoustic impedance meter. In this diagram and the subsequent Figures, common electronic circuits, e.g., oscillators, operational amplifiers, precision rectifiers and the like, will not be described in detail, since any of many suitable arrangements will perform satisfactorily in my invention. The oscillator 21, generates a 220 Hz sine wave of fixed amplitude and stable frequency. The choice of frequency is not critical, though best performance is obtained with frequencies below approximately 600 Hz and results published in the literature generally mentions the use of 220 Hz. The modulator 22, which may be a DC-controlled electronic attenuator, drives the final amplifier 23, and the modulated 220 Hz current actuates a miniature loudspeaker 16a, in the transducer assembly 16. The resulting 220 Hz sound pressure is coupled, by means of the flexible tube 17b, to the ear probe 17, and thence to the subject's ear canal. A sample of the ear canal sound pressure is conducted, by means of the ear probe 17, and a second flexible tube 17c, to a miniature microphone 16b, located in the transducer assembly 16. The low-level microphone voltage is amplified by the band-pass amplifier 24, which will be discussed in detail later, and is converted to pulsating full-wave rectified positive dc voltage 25a, by the precision rectifier circuit 25. The operational amplifier 26, compares a current, determined by the resistor 26a, and the positive voltage 25a, with a negative current derived by the resistor 26b, from the negative regulated voltage 26c. Since the operational amplifier 26, is operating without a DC negative feedback path, its gain is extremely high and small unbalances which may exist between the sound-pressure-dependent positive current flowing in resistor 26a, and the negative reference current, flowing in resistor 26b, result in large excursions in the voltage 26d, at the amplifier output. The Zener diode 26e, maintains this voltage within the limits of normal operation of the modulator 22, while the capacitor 26f, introduces a time constant in the control loop for improved stability. By employing the output voltage 26d, as a control voltage for the modulator 22, the feedback loop is closed and stability is achieved. This overall control system is the means for automatically and continuously maintaining the compliance test sound at a constant level, regardless of compliance, and is novel to my invention.

Constant sound pressure in the ear canal, as sensed by the microphone 16b, and controlled by the aforesaid feedback loop, causes the output of the amplifier 23 to be proportional to the equivalent volume, or compliance, of the ear canal under test. Thus, the voltage 23a, is a measure of the ear canal compliance. An operational amplifier 27, has as its output voltage 27a, a multiple of the voltage 23a as determined by the relative values of the resistors 27b, 27c, and 11a. The resistor 11a is one of the aforementioned calibration adjustments, allowing the voltage 27a, to be adjusted, over a limited range, to compensate for component variations. The output voltage 27a, of the operational amplifier 27, is converted to negative full-wave rectified pulsating DC at the output 28a, of the precision rectifier circuit 28. Operational amplifier 29 has an output voltage 29a, in accordance with the relative values of the resistors 29b, 29c, and 29d and the setting of the aforementioned calibration potentiometer 11b, used to compensate for component variations. The resulting output voltage 29a, is filtered to essentially pure DC by the action of the capacitor 29e, and is proportional to the ear canal compliance. I therefore designate it as the voltage $E_c$. In this embodiment of my invention, I have scaled this $E_c$ voltage 29a, at +1.00v DC per cubic centimeter of ear canal compliance. While this is a convenient scale factor, others could be used with equal success. This is the means for automatically and continuously deriving an electrical voltage which is an analog of compliance, thereby measuring compliance, and is novel to my invention.

A conventional digital voltmeter 5, which is selected to read from 0.00 to +9.99v DC in 0.01v increments, displays the $E_c$ voltage and reads in cubic centimeters of compliance directly, in convenient digital form. This is the means for automatically and continuously displaying the measured compliance as a digital quantity and is novel to my invention.

Alternatively, a conventional moving pointer meter display 5a, may be employed, though resolution is degraded. The $E_c$ voltage is also made available to accessory apparatus, such as an X-Y plotter, for convenient recording of test results.

A unity-gain operational amplifier 30, employing resistors 30b and 30c, inverts the $E_c$ voltage 29a, to its negative equivalent $-E_c$ at the output 30a, of amplifier 30. In the unactuated position of the stimulus switch 7, the switch section 7b, directly connects the voltage 30a, to the capacitor 31. The output 32a, of the voltage follower 32, is the $-E_c$ voltage when the switch 7 is unactuated. The output 33a of the operational amplifier 33, is zero by virtue of the chosen equality of the two input resistors 33b and 33c and the negative equivalency of the $-E_c$ voltage 32a, with the $E_c$ voltage 29a. Resistor 33d, is the feedback resistor for amplifier 33, and the output voltage 33a is applied to meter 6, which may be zero offset to the right in order to achieve maximum scale utilization. When the stimulus switch 7, is actuated, section 7a, closes and section 7b, disconnects the $-E_c$ voltage 30a, from the capacitor 31, which remains charged to the voltage last present prior to actuation of switch 7. Since the normal acoustic reflex is in the direction of a reduced compliance, the voltage 29a, may be expected to decrease by approximately 5mv DC, equivalent to a compliance decrease of 0.005 cc, and less than the reliable readout capability of the digital voltmeter 5. However, this decrease in the $E_c$ voltage 29a, disturbs the equivalency between it and the stored $-E_c$ voltage 32a. The difference current is sensed by the amplifier 33, which, in turn, produces an amplified $-dE_c$ output voltage 33a, proportional to the change in compliance while the switch 7, is actuated, i.e., while the contra-lateral stimulus is present. The meter 6, which may be calibrated in increments of 0.005 cc compliance change, deflects in accordance with the acoustic reflex stiffening of the tympanic membrane. This is the means for automatically measuring the change in compliance due to the acoustic reflex in the presence of acoustic stimulus, and storage means for comparing the pre-stimulus and post-stimulus compliances, and is novel to my invention.

The pump 3, is a compressible corrugated bellows driven by a screw 3a, which in turn is coupled to a multi-turn potentiometer 3b. The output voltage 34a, of the voltage follower 34, is a function of pump screw position, and after processing by the operational amplifier 35, employing resistors 35b and 35c, becomes a voltage 35a, proportional to pump position. The enclosed volume of the pump is very large compared with other system components, thereby permitting a convenient mechanical relationship between pump screw position and internal pump pressure, if the pressure release value 20 is pressed and released at a preestablished position of the pump screw 3a. By design component selection, the $E_p$ voltage 35a can be scaled to a convenient +1.00v DC per 100mm $H_2O$ pressure, and may be used by accessory apparatus, such as an X-Y plotter for data recording. Discussion of the stimulus generator 36 follows in connection with FIG. 7. The power supply 37 shown in FIG. 2 is of conventional I-C regulated design using readily available components.

The Transducer assembly 16, is detailed in FIG. 3. A miniature loudspeaker 16a, within the transducer assembly 16, serves as a sound source and is coupled, by means of a flexible tube 17b, to the ear probe 17, and thence to the ear canal, shown schematically as the cavity 38. Sound pressure in the ear canal cavity 38 is conducted, by means of the ear probe 17, and flexible tube 17c to a miniature microphone 16b. A communicating passage 16c couples the loudspeaker 16a to a coil of capillary tubing 16d, which, by means of the long flexible tube 19a, the headset pressure plug 19, and receptacle 13, connects to the pump 3.

A Transducer Equivalent Circuit FIG. 4 is an electrical analog of the pressure system and transducer assembly and permits consideration of the interaction of the various elements, using resistors of various values for the tubing and microphone and capacitors in place of the various enclosed volumes. The sound source 16a, can be considered as a voltage source $E_1$, feeding two R-C branches with currents $I_1$ and $I_2$. The acoustic resistance of the capillary tubing 16d, is several orders of magnitude greater than either of the flexible tubes 17b, and 17c or the diaphragm structure of the microphone 16b. The acoustic resistance of diaphragm structure of the microphone 16b, is large compared with that of the tubing 17b and 17c. The pump volume 3, is very large compared to the cavity 38, and the tubing 19a, is comparable to tubing 17b or 17c. It can readily be shown that, as a result of these various acoustic resistances, undesired current $I_2$, flowing thru the pump system, is insignificant with respect to the desired current, $I_1$, and that the voltage $E_3$, at the microphone, is approximately the ear canal voltage $E_2$, while the pump voltage $E_4$, produced by the insignificant current $I_2$, has no degrading effect on the ability of the microphone to measure the sound pressure in the ear canal. My experiments have shown that, due to the high degree of isolation achieved between the pump system and the ear canal, measurements of ear canal compliance are unaffected by capping the tube 16d, venting it the ambient air or connecting it to the pump system thru tube 19a. This is the means to acoustically isolate the transducer assembly from the pump assembly, thereby permitting the use of a "2-tube" ear probe, and is novel to my invention.

The microphone channel Band-Pass Amplifier 24, is detailed in FIG. 6. A voltage follower 24a provides a high-impedance load for the microphone and a low-impedance source for the subsequent amplifiers 24b and 24d. The partial schematic 39 of FIG. 5 depicts a multiple-feedback, infinite gain, Band-Pass Active Filter circuit of Conventional design. In this circuit, the two capacitors C, are normally of equal value, and the center frequency, gain and bandwidth of the active filter amplifier depend on a complex relationship between all three resistors and both capacitors. The limited selection of inexpensive capacitors makes it impractical to predesign gain and bandwidth in such a filter and then set the center frequency by capacitor selection. In the Tunable band-pass active filter circuit used in my invention, partial schematic 40, and 24b, 24d, I make use of commercial 10% tolerance capacitors and achieve precise tuning of the center frequency of the filter by means of the potentiometer $R_o$. I select one of the feedback capacitors $C_o$, as 5/4 of the normal design value C, and drive it with an adjustable voltage of the same phase as the filter output. This allows adjustment of the reactive current flowing thru the 5/4 value capacitor just as though the capacitor itself were adjustable, thereby tuning the filter to a precise center frequency without disturbance of the band-width and gain parameters. A typical band-pass filter has a response curve 41, with center frequency $f_o$, bandwidth BW, at the −3dB points as indicated. In my 2-stage active filter band-pass amplifier, I use two such stages, stagger-tuned to achieve a flat-topped response curve with sharp attenuation outside of the pass band. Each band-pass stage has a gain of 10 and a 14 Hz bandwidth. The first stage 24b, is adjusted to peak at 213 Hz by means of potentiometer 24c, and when so tuned has a response curve similar to 42a. The second stage 24d, is adjusted to peak at 227 Hz by means of potentiometer 24e, and when so tuned, has a response curve similar to curve 42b. The cascaded combination of the two stages 24b, and 24d exhibits a flat-topped, sharp-skirted response similar to curve 42c. Between 214 Hz and 226 Hz this composite response is flat to less than ±0.05dB. The −3dB bandwidth is 211 Hz to 229 Hz and attenuation, beyond the pass band, is approximately −120dB per octave. This highly selective, tunable, active filter, bandpass amplifier is critical to the suppression of the interfering effects of subject's breathing, pulse and head movement. This is the means for very narrow bandwidth amplification, employing tunable active filter means, and is novel to my invention.

The Stimulus System 36 of my electro-acoustic impedance meter is depicted in FIGS. 7 and 2. I use a dual multivibrator 36a as the frequency determined oscillator, with resistor 36b, adjustable over a limited range to set the center frequency to 4KHz. A conventional divide-by-16 counter 36c, then derives 2 KHz, 1 KHz, 500 Hz and 250 Hz from the generated 4 KHz. The outputs of multivibrator 36a, and divider 36c, are approximate square waves. Active filter amplifiers, of conventional design, are employed to select the fundamental component from the generated square waves. I have found that a bandwidth of 10% of center frequency is sufficient to suppress the third harmonic content to less than the 2% permitted under current audiometer specifications. A square wave contains no second or fourth harmonic. The 1 KHz filter 36f, is typical for the other filters 36d, 36e, 36g, and 36h, and each contains an adjustable potentiometer for setting the stimulus level. The desired stimulus frequency is selected by means of the frequency switch 8. Field effect transistor 36i, in conjunction with the bias and time delay network 36j, control application of the selected stimulus frequency to the final amplifier 36k in response to the actuation of the stimulus switch 7a. Attenuator 9, is of conventional resistive ladder type and controls the level of stimulus at the earphone 15. The attenuator range is from 0 to +125dB HL, but is limited to 110dB HL at 250 Hz, and the stimulus tone level and quality, and the rise and decay rates permit this section of my instrument to be used as a screening audiometer as well as for contra-lateral stimulus of the acoustic reflex. This is the means for producing an acoustic stimulus, including means for generating a series of harmonically-related sinusoidal electrical voltages from a single square wave oscillator, and is novel to my invention.

To summarize the major points of my invention, I have described and explained the function of several means which are important to my invention and which are believed to be novel in concept and/or application, briefly these are:

1. Means for automatically and continuously maintaining the compliance test sound at a constant level, regardless of compliance.

2. Means for automatically and continously deriving an electrical voltage which is an analog of compliance, thereby measuring compliance.

3. Means for automatically and continously displaying the measured compliance as a digital quantity.

4. Means for automatically measuring the change of compliance due to the acoustic reflex in the presence of acoustic stimulus, and storage means to compare the pre-stimulus and post-stimulus compliances.

5. Means to acoustically isolate the transducer assembly from the pump assembly, thereby permitting the use of a "2 tube" ear probe.

6. Means for achieving very narrow bandwidth amplification, employing tunable active filter means.

7. Means for producing an acoustic stimulus, including means for generating a series of harmonically-related sinusoidal voltages from a single oscillator.

I claim:

1. An automatic acoustic impedance meter apparatus for evaluating the middle ear and tympanic membrane system, said apparatus being comprised of:
   sound source means, including oscillator means, modulator means, amplifier means and loudspeaker means, operationally interconnected;
   sound sensor means, including microphone means, narrow-band amplifier means and rectifier means, operationally interconnected;
   ear probe means for insertion in the subject's ear canal, including flexible probe tip pressure sealing means, tubular interconnecting means for acoustically connecting said sound source means and said sound sensor means to said ear probe means and thereby to the subject's ear canal;
   inverse feedback means, including reference means and amplifier means to control said sound source means in response to the ear canal sound level sensed by said sound sensor means, thereby maintaining an unchanging sound level in the subject's ear canal regardless of the compliance thereof;
   measurement means, including compliance analog voltage determining means responsive to the electrical excitation of said loud-speaker means, thereby obtaining a compliance analog voltage representative of the subject's ear canal compliance and including voltmeter means to measure said compliance analog voltage as a measure of the subject's ear canal compliance.

2. Apparatus as set forth in claim 1 and including:
   pump means connected to said ear probe means for pressurizing or evacuating the subject's ear canal during testing;
   pressure indicating means, operationally connected to said pump means, including gauge means for determining existing pressure in the subject's ear canal;
   acoustic isolation means, including capillary tube means interposed between said pump means and aforesaid ear probe means, to acoustically isolate said pump means from said sound source means and said sound sensor means, thereby permitting improved ear canal compliance evaluation.

3. Apparatus as set forth in claim 1 and including:
   acoustic stimulus means, including earphone means, oscillator means, amplifier means, switching means and attenuator means operationally interconnected to generate and control an acoustic stimulus.

4. Apparatus as set forth in claim 1 and including:
   narrow-band filter means, including a plurality of tunable active filters operationally interconnected to obtain a sharp-skirted, flat-topped filter passband response.

5. Apparatus as set forth in claim 3 and including:
   storage means operationally interconnected to said compliance analog voltage means for retaining a sample of said compliance analog voltage, thereby obtaining a stored compliance analog voltage;
   comparison means, including connected amplifier means, to determine the difference between said stored compliance analog voltage and an existing compliance analog voltage, thereby obtaining a compliance difference analog voltage;
   switching means controlling said storage means and said comparison means to obtain a compliance difference analog voltage during acoustic stimulus, said compliance difference analog voltage during acoustic stimulus being representative of the acoustic reflex response during acoustic stimulus.

* * * * *